US012746263B2

(12) United States Patent
Chin

(10) Patent No.: US 12,746,263 B2
(45) Date of Patent: Sep. 29, 2026

(54) **COMPOSITION FOR TREATMENT OF AUTOIMMUNE DISEASES COMPRISING *Lactobacillus sakei* OR EXTRACELLULAR VESICLES DERIVED THEREFROM AS ACTIVE INGREDIENT**

(71) Applicant: LISCURE BIOSCIENCES INC., Seongnam-si (KR)

(72) Inventor: Hwa Sup Chin, Seoul (KR)

(73) Assignee: LISCURE BIOSCIENCES INC., Seongnam-si (KR)

( * ) Notice: Subject to any disclaimer, the term of this patent is extended or adjusted under 35 U.S.C. 154(b) by 216 days.

(21) Appl. No.: 18/575,198

(22) PCT Filed: Jul. 6, 2022

(86) PCT No.: PCT/KR2022/009760
§ 371 (c)(1),
(2) Date: Dec. 28, 2023

(87) PCT Pub. No.: WO2023/282622
PCT Pub. Date: Jan. 12, 2023

(65) Prior Publication Data

US 2024/0325468 A1 Oct. 3, 2024

(30) Foreign Application Priority Data

Jul. 7, 2021 (KR) ........................ 10-2021-0088901
Jul. 5, 2022 (KR) ........................ 10-2022-0082279

(51) Int. Cl.
*A61K 35/747* (2015.01)
*A61P 37/06* (2006.01)
*C12N 1/205* (2026.01)
*C12R 1/225* (2006.01)

(52) U.S. Cl.
CPC ............ *A61K 35/747* (2013.01); *A61P 37/06* (2018.01); *C12N 1/205* (2021.05); *C12R 2001/225* (2021.05)

(58) Field of Classification Search
None
See application file for complete search history.

(56) References Cited

U.S. PATENT DOCUMENTS 8,034,606 B2 * 10/2011 Park ..................... A61K 35/747
435/252.9
2022/0151253 A1 5/2022 Choi et al.

FOREIGN PATENT DOCUMENTS

| | | | |
|---|---|---|---|
| KR | 10-2012-0100608 | A | 9/2012 |
| KR | 10-2020-0020775 | A | 2/2020 |
| KR | 10-2020-0058849 | A | 5/2020 |
| KR | 10-2123505 | B1 | 6/2020 |
| KR | 10-2021-0031301 | A | 3/2021 |
| KR | 10-2269961 | B1 | 6/2021 |
| KR | 10-2022-0091427 | A | 6/2022 |

OTHER PUBLICATIONS

Yamasaki-Yashiki et al., Bioscience of Microbiota, Food and Health (2019), 38(1), pp. 23-29.*

Jhun et al., "*Lactobacillus sakei* suppresses collagen-induced arthritis and modulates the differentiation of T helper 17 cells and regulatory B cells", Journal of Translational Medicine, vol. 18, No. 317, 2020, pp. 1-11, https://doi.org/10.1186/s12967-020-02477-8.

Katerina Hiozkova et al., "Assessment of the Metabolic Profile of Primary Leukemia Cells", Journal of Visualized Experiments, Nov. 2018, vol. 141, pp. 1 through 7.

Guillame Van Niel et al., "Shedding light on the cell biology of extracellular vesicles", Nature Reviews: Molecular Cell Biology, Jan. 2018, pp. 1-17.

International Search Report for PCT/KR2022/009760 dated Oct. 12, 2022.

Rather et al., "Probiotic *Lactobacillus sakei* proBio-65 Extract Ameliorates the Severity of Imiquimod Induced Psoriasis-Like Skin Inflammation in a Mouse Model", Frontiers in Microbiology, vol. 9, Article 1021, May 17, 2018, pp. 1-11.

* cited by examiner

*Primary Examiner* — Brian J Davis
(74) *Attorney, Agent, or Firm* — Sughrue Mion, PLLC

(57) ABSTRACT

The present disclosure relates to a composition containing *Lactobacillus sakei* or extracellular vesicles derived therefrom. The present disclosure also relates to a novel *Lactobacillus sakei* LBML6 strain. The *Lactobacillus sakei* according to the present disclosure is a strain which has inhibitory activity against TNFα and IgG in blood and in which the proportion of tolDC cells and Treg cells is increased, and can be used for various applications such as the prevention, alleviation and/or treatment of autoimmune disease in human or animals as well as intestinal regulation.

7 Claims, 10 Drawing Sheets

COMPOSITION FOR TREATMENT OF AUTOIMMUNE DISEASES COMPRISING *Lactobacillus sakei* OR EXTRACELLULAR VESICLES DERIVED THEREFROM AS ACTIVE INGREDIENT This Application is a National Stage of International Application No. PCT/KR2022/009760 filed Jul. 6, 2022, claiming priority based on Korean Patent Application No. 10-2021-0088901 filed Jul. 7, 2021 and Korean Patent Application No. 10-2022-0082279 filed Jul. 5, 2022.

TECHNICAL FIELD

The present disclosure relates to a composition for preventing, alleviating or treating an autoimmune disease, which contains *Lactobacillus sakei*, a culture, lysate, extract or fermentation product thereof or extracellular vesicles isolated therefrom as an active ingredient.

BACKGROUND ART

Autoimmune diseases are diseases that occur when the body's immune function attacks itself. It is commonly formed over a long period of time. Symptoms persist chronically and usually result in permanent damage to organs, and there is almost no cure. Although knowledge about autoimmune diseases has advanced significantly over a long period of time, the exact mechanism of onset, the identity of self-antigens, regulatory genetic factors, etc. are still unclear. Autoimmune diseases can be largely divided into organ-specific diseases and systemic diseases.

The organ-specific autoimmune disease occurs as a result of immune response against organ-specific antigens and can occur in almost all organs in the body. The systemic autoimmune disease is not caused by an immune response against specific cells but by an immune response against antigens expressed throughout the body. The systemic autoimmune disease can also occur selectively in specific organs.

Examples of the autoimmune disease include asthma, atopic dermatitis, psoriatic dermatitis, allergic rhinitis, allergic conjunctivitis, urticaria, etc., which are known to cause clinical symptoms by causing damage and abnormities of body organs due to allergic reactions. In addition, rheumatoid arthritis and lupus known to occur due to hypersensitivity reactions (including autoantibody responses) to self-proteins (self-antigens such as immunoglobulin, collagen, DNA, etc.) (Vaughan J H. *Med Times* 1969; 97:187-204) are included. It is known that the lupus, rheumatoid arthritis, etc. cause damage and inflammation in specific organs by antigen-specific IgG antibodies that react with antigens present in the body (self-antigens) owing to hypersensitivity to the self-proteins. Therefore, they are classified as autoimmune diseases.

The direct cause of autoimmune diseases has not been clearly identified yet and various therapeutic agents such as steroids, non-steroidal anti-inflammatory drugs, immunosuppressants, etc. are used to treat the autoimmune diseases. However, these therapeutic agents do not show fundamental therapeutic effects and their use is limited due to various side effects. Additionally, some chemotherapy drugs have drawbacks such as lack of efficacy against autoimmune diseases that have occurred already.

Therefore, there is a need to develop a therapeutic agent for an autoimmune disease, which is effective in relieving inflammatory symptoms and pain and easy to take while having fewer side effects.

The above description in the background art section is only for the purpose of improving the understanding of the present disclosure and it should not be taken as an admission that it is already known to those having ordinary knowledge in the related art.

DISCLOSURE

Technical Problem

The inventors of the present disclosure have made efforts to find a *lactobacillus* strain applicable to various autoimmune diseases including rheumatoid arthritis. As a result, they have identified that *Lactobacillus sakei* or a culture thereof has an effect of preventing or treating an autoimmune disease by suppressing proinflammatory factors that cause various autoimmune diseases or increasing the proportion of immunosuppressive cells and have completed the present disclosure.

The present disclosure is directed to providing a composition for preventing, alleviating or treating an autoimmune disease, which contains *Lactobacillus sakei*, a culture, lysate, extract or fermentation product thereof; or extracellular vesicles derived from the *Lactobacillus sakei*; as an active ingredient.

The present disclosure is also directed to providing a method for preventing, alleviating or treating an autoimmune disease, which includes administering a therapeutically effective amount of: *Lactobacillus sakei*, a culture, lysate, extract or fermentation product thereof; or extracellular vesicles derived from the *Lactobacillus sakei*; to a subject in need thereof.

The present disclosure is also directed to providing a therapeutic use of *Lactobacillus sakei* or a culture, lysate, extract or fermentation product thereof.

The present disclosure is also directed to providing a therapeutic use of extracellular vesicles derived from *Lactobacillus sakei* or a culture, lysate, extract or fermentation product thereof.

The present disclosure is also directed to providing a method for preparing a composition for preventing, alleviating or treating an autoimmune disease.

The present disclosure is also directed to providing a *Lactobacillus sakei* LBML6 strain deposited with the accession number KCCM13011P.

Other purposes and advantages of the present disclosure will become more apparent by the following detailed description, claims and drawings.

Technical Solution

In an aspect, the present disclosure provides a composition for preventing, alleviating or treating an autoimmune disease, which contains: *Lactobacillus sakei*, a culture, lysate, extract or fermentation product thereof; or extracellular vesicles derived from the *Lactobacillus sakei*; as an active ingredient.

Specifically, the *Lactobacillus sakei* strain that can be used in the present disclosure includes a *Lactobacillus sakei* LBML6 strain deposited in the Korean Culture Center of Microorganisms with the accession number KCCM13011P, a *Lactobacillus sakei* WIKIM31 strain deposited with the accession number KCCM12654P or a *Lactobacillus sakei* WIKIM0109 strain deposited in the Korean Collection for Type Cultures with the accession number KCTC13818BP, although not being limited thereto. Most specifically, the *Lactobacillus sakei* LBML6 strain may be used.

In another aspect, the present disclosure provides the *Lactobacillus sakei* LBML6 strain deposited with the accession number KCCM13011P.

The *Lactobacillus sakei* contained in the composition according to the present disclosure may be in the form of live or dead cells and may also exist in dry or freeze-dried form. The forms and formulation methods of *lactobacillus* suitable for inclusion in various compositions are well known to those skilled in the art. For example, the *Lactobacillus sakei* may be formulated into a culture obtained by culturing in a known liquid medium or solid medium, a fermentation product obtained by culturing the strain together with additional ingredients, an extract obtained by extracting the strain with an organic solvent, a lysate obtained by lysing, crushing or homogenizing the cell membrane of the strain, etc., although not being limited thereto.

In a specific exemplary embodiment, the composition may be a composition containing the *Lactobacillus sakei* strain in the form of live or dead cells.

In another specific exemplary embodiment, the composition may be a composition containing the culture, lysate, extract or fermentation product of the *Lactobacillus sakei* strain.

In another specific exemplary embodiment, the composition may be a composition containing extracellular vesicles derived from *Lactobacillus sakei* or a culture, lysate, extract or fermentation product thereof.

Extracellular vesicles (EVs) allow exchange of substances (proteins, lipids and genetic materials) between cells and function as mediators of physiological/pathological signaling. The extracellular vesicles are largely classified into exosomes and microvesicles. The exosomes have various sizes depending on their origin. They are intraluminal vesicles formed by inward budding of the endosomal membrane during maturation of multi-vesicular endosomes and are secreted upon fusion of the multi-vesicular endosomes with cell surface. The microvesicles are vesicles with a size of 10-1000 nm that are released from the plasma membrane. Individual cells produce different extracellular vesicles depending on physiological conditions and secret extracellular vesicles having specific lipid/protein/nucleic acid compositions (Jae-Wook Lee (2019). Shedding light on the cell biology of extracellular vesicles. *BRIC View* 2019-R03).

In the present specification, the term "extracellular vesicles" encompasses the exosomes and microvesicles.

The exosomes or extracellular vesicles have various diameters in a range of about 1-1,000 nm, specifically 10-1,000 nm, more specifically 10-800 nm, most specifically 20-600 nm.

The exosomes or extracellular vesicles contained in the composition of the present disclosure are included in large quantities in a culture (e.g., a supernatant of the culture) of *Lactobacillus sakei.*

Since the exosomes or extracellular vesicles are included in large quantities in a culture (e.g., a supernatant of the culture) of *Lactobacillus sakei*, the exosomes or extracellular vesicles isolated and purified therefrom may be utilized as a therapeutic agent on its own, or a culture, lysate, extract or a fermentation product containing the exosomes or extracellular vesicles in large quantities may be utilized as a therapeutic agent.

In the present specification, the term "isolation" includes not only a process of selectively obtaining a desired substance (e.g., exosomes) from a biological sample (e.g., a *Lactobacillus sakei* culture) (positive isolation) but also a process of selectively removing impurities other than the desired substance (negative isolation). Therefore, the term "isolation" may be used with the same meaning as "obtainment", "extraction" or "purification". In the present disclosure, the isolation of exosomes or extracellular vesicles may be performed by any method commonly employed in the art without limitation. For example, a commercially available exosome isolation kit (e.g., EXO-BB, ExoQuick®-ULTRA, ExoQuick®-TC, Capturem™ exosome isolation kit, total exosome isolation kit, ExoTrap™ exosome isolation spin column kit, Exo2D™, etc.) may be utilized, or separation based on the difference in the specific gravity of ingredients in a solution (e.g., centrifugation), separation based on size (e.g., ultrafiltration or vacuum filtration) or separation based on the affinity for a specific substrate (e.g., affinity chromatography) may be included. However, any separation method based on the intrinsic physical properties of a desired substance in a nonhomogeneous sample commonly used in the art may be used without limitation.

In a specific exemplary embodiment of the present disclosure, the autoimmune disease is selected from a group consisting of atopic dermatitis, psoriatic dermatitis, alopecia areata, allergy, asthma, conjunctivitis, periodontitis, rhinitis, otitis media, pharyngitis, tonsillitis, Crohn's disease, inflammatory colitis, ankylosing spondylitis, lupus, psoriatic arthritis, osteoarthritis, rheumatoid arthritis, periarthritis of shoulder, tendonitis and multiple sclerosis.

Since the *Lactobacillus sakei*, the culture, lysate, extract or fermentation product thereof; or the extracellular vesicles derived from *Lactobacillus sakei* or a culture, lysate, extract or fermentation product thereof of the present disclosure inhibit proinflammatory factors that cause various autoimmune diseases (e.g., TNF$\alpha$, autoantibodies, collagen, antigen-specific IgGs, etc.) or increase the proportion of immunosuppressive cells (e.g., tolDC cells, Tregs, etc.), they can be used effectively for the prevention or treatment of autoimmune diseases.

In a specific exemplary embodiment of the present disclosure, the composition is a pharmaceutical composition.

In another aspect, the present disclosure provides a method for preventing, alleviating or treating an autoimmune disease, which includes administering a therapeutically effective amount of *Lactobacillus sakei*, a culture, lysate, extract or fermentation product thereof; or extracellular vesicles derived from the *Lactobacillus sakei* or the culture, lysate, extract or fermentation product thereof to a subject in need thereof.

In another aspect, the present disclosure provides a therapeutic use of *Lactobacillus sakei* or a culture, lysate, extract or fermentation product thereof.

In another aspect, the present disclosure provides a therapeutic use of extracellular vesicles derived from *Lactobacillus sakei* or a culture, lysate, extract or fermentation product thereof.

In a specific exemplary embodiment of the present disclosure, the therapeutic use is a use for prevention, alleviation or treatment of an autoimmune disease.

The term "subject" used herein refers to a mammal which is the subject of treatment, monitoring or experiment. Specifically, it may be human or an animal in need of the prevention, alleviation and/or treatment of an autoimmune disease.

The pharmaceutical composition according to the present disclosure may be administered orally or parenterally.

The parenteral administration can be achieved, for example, by intravenous injection, transdermal administration, subcutaneous injection, intramuscular injection, intravitreal injection, eye drop administration, intracerebroventricular injection, intrathecal injection, intraamniotic injection, intraarterial injection, intraarticular injection, intracardiac injection, intracavernous injection, intracerebral injection, intracisternal injection, intracoronary injection, intracranial injection, intradural injection, epidural injection, intrahippocampal injection, intranasal injection, intraosseous injection, intraperitoneal injection, intrapleural injection, intraspinal injection, intrathoracic injection, intrathymic injection, intrauterine injection, intravaginal injection, intraventricular injection, intravesical injection, subconjunctival injection, intratumoral injection, topical injection, etc.

The pharmaceutical composition of the present disclosure may contain a pharmaceutically acceptable carrier. In the present disclosure, the term "pharmaceutically acceptable carrier" refers to a carrier or diluent which does not cause significant irritation to an organism and does not abrogate the biological activity and properties of the administered ingredient. In the present disclosure, the pharmaceutically acceptable carrier may be one or more of saline, sterile water, Ringer's solution, buffered saline, dextrose solution, maltodextrin solution, glycerol and ethanol. If necessary, an injectable formulation suitable for injection to tissues or organs may be prepared by adding commonly used other additives such as an antioxidant, a buffer, a bacteriostat, etc. In addition, it can be formulated into a dried preparation (particularly, a freeze-dried preparation) that can be prepared into an injectable solution by adding an isotonic sterile solution or, in some cases, sterile water or physiological saline. In addition, a target organ-specific antibody or ligand can be bound to the carrier so as to allow specific action on the target organ. Suitable preparations well known in the art are disclosed in Remington's Pharmaceutical Science (Mack Publishing Company, Easton PA).

Specifically, the composition of the present disclosure may further contain a filler, an excipient, a disintegrant, a binder, a glidant, etc. In addition, the composition of the present disclosure may be formulated by a method well known in the art so as to provide quick, sustained or delayed release of the active ingredient after administration to a mammal.

In the present specification, the "administration" refers introduction of the composition of the present disclosure to a patient by any suitable means. The composition of the present disclosure may be administered through various oral or parenteral routes as long as it can reach the target tissue.

For example, the composition of the present disclosure may be administered clinically by intramuscular, intravenous or intraperitoneal injection.

For injection, it may be specifically formulated into a pharmaceutically suitable buffer such as Hank's solution, Ringer's solution or buffered physiological saline. For transmucosal administration, a penetrant suitable for the corresponding barrier is used. Such penetrants are generally known in the art.

Formulations for parenteral administration include a sterilized aqueous solution, a nonaqueous solution, a suspension, an emulsion, etc. For the nonaqueous solution or suspension, propylene glycol, polyethylene glycol, vegetable oil such as olive oil, an injectable ester such as ethyl oleate, etc. may be used.

In the present specification, the "effective amount" refers to an amount necessary to delay or completely stop the onset or progress of a specific disease desired to be treated, and the effective amount of *Lactobacillus sakei* contained in the pharmaceutical composition of the present disclosure means the amount required to achieve the effect of preventing, ameliorating or treating an autoimmune disease. Accordingly, the effective amount may be controlled depending on various factors including the kind of the disease, the severity of the disease, the kinds and contents of other ingredients contained in the composition, the age, body weight, general health condition and diet of a patient, administration time, administration route, treatment period, and co-administered drugs. It is obvious to those skilled in the art that an appropriate daily administration dosage can be determined adequately by a physician.

For the purpose of the present disclosure, it is desired that the therapeutically effective amount for a particular patient is varied depending on various factors such as the response desired to be achieved, the particular composition, the age, body weight, general health condition, sex and diet of a patient, administration time, administration route, the excretion rate of the composition, treatment period, and co-administered drugs, and other similar factors well known in the medical field.

In the present specification, the "treatment" refers to an approach to achieve a favorable or desired clinical result. For the purpose of the present disclosure, the favorable or desired clinical result includes nonrestrictively the amelioration of symptoms, the reduction of the scope of diseases, the stabilization (i.e., prevention of aggravation) of disease state, the delay or slowing of disease progress, and the amelioration or temporary alleviation and reduction of disease state (partially or completely). In addition, the "treatment" may also mean increasing survival rate as compared to that expected when the treatment is not given. The "treatment" includes both therapeutic treatment and preventive measure. The treatment includes the treatment of not only a disorder to be prevented but also a disorder that has occurred already. The "alleviation" of a disease refers to the reduction of the scope of disease state and/or undesired clinical symptoms and/or the delay or extension of the time course of progress as compared to the absence of the treatment.

In a specific exemplary embodiment of the present disclosure, the composition of the present disclosure is a food composition.

*Lactobacillus sakei*, a culture, lysate, extract or fermentation product thereof, or extracellular vesicles derived from *Lactobacillus sakei* or a culture, lysate, extract or fermentation product thereof contained in the food composition of the present disclosure are the same as described above.

When the composition of the present disclosure is used as a food composition, the food composition may be in the form of a functional health food, a condiment, a beverage, a bar, etc. In addition, the food composition containing the strain as an active ingredient may be a beverage such as fermented milk, etc. Therefore, the present disclosure provides a *lactobacillus* starter for fermenting food, which contains *Lactobacillus sakei* or a culture thereof.

The food composition of the present disclosure may be prepared using, in addition to the active ingredient, a sitologically suitable and physiologically acceptable adjuvant. The adjuvant may be an excipient, a disintegrant, a sweetener, a binder, a coating agent, a swelling agent, a lubricant, a glidant, a flavorant, etc.

Specifically, the food composition may be prepared using one or more sitologically acceptable carrier in addition to the active ingredient described above.

For example, for preparation of a tablet or a capsule, the active ingredient may be bound with an oral, nontoxic, pharmaceutically acceptable inert carrier such as ethanol, glycerol, water, etc. In addition, if desired or necessary, a suitable binder, lubricant, disintegrant and coloring agent may also be added. Suitable binders include natural sugar such as starch, gelatin, glucose or ß-lactose, corn sweetener, natural or synthetic gum such as acacia, tragacanth or sodium oleate, sodium stearate, magnesium stearate, sodium benzoate, sodium acetate, sodium chloride, etc., although not being limited thereto. The disintegrant includes starch, methyl cellulose, agar, bentonite, xanthan gum, etc., although not being limited thereto. When the composition is prepared as a liquid solution, one or more of saline, sterile water, Ringer's solution, buffered saline, albumin injection, dextrose solution, maltodextrin solution, glycerol and ethanol may be used as an acceptable pharmaceutical carrier and, if necessary, other common additives such as an antioxidant, a buffer, a bacteriostat, etc. may be used. In addition, an injectable formulation such as an aqueous solution, a suspension, an emulsion, etc., a pill, a capsule, a granule, or a tablet may be prepared by further adding a diluent, a dispersant, a surfactant, a binder or a lubricant.

The food composition according to the present disclosure may be added to various foods. The foods to which the composition of the present disclosure may be added include, for example, beverages, vitamin complexes, health supplements, etc.

The food composition of the present disclosure may contain the ingredients commonly used for preparation of food, e.g., a protein, a carbohydrate, a fat, a nutrient, a seasoning agent and a flavorant. Examples of the carbohydrate include common sugars such as monosaccharides, e.g., glucose, fructose, etc., disaccharides, e.g., maltose, sucrose, oligosaccharide, etc. and polysaccharides, e.g., dextrin, cyclodextrin, etc. and sugar alcohols such as xylitol, sorbitol, erythritol, etc. Examples of the flavorant include natural flavorants [thaumatin, stevia extract (e.g., rebaudioside A, glycyrrhizin, etc.)] and synthetic flavorants (saccharin, aspartame, etc.). For example, when the food composition of the present disclosure is prepared as a drink or a beverage, it may further contain citric acid, fructose syrup, sugar, glucose, acetic acid, malic acid, fruit juice, plant extracts, etc.

In another aspect, the present disclosure provides a feed additive or a feed containing *Lactobacillus sakei*, a culture, lysate, extract or fermentation product thereof, or extracellular vesicles derived from *Lactobacillus sakei* or a culture, lysate, extract or fermentation product thereof as an active ingredient.

When used as a feed additive, the composition may be prepared in the form of a 20-90% concentrate, powder or granule. The feed additive may further contain one or more of an organic acid such as citric acid, fumaric acid, adipic acid, lactic acid, malic acid, etc., a phosphate such as sodium phosphate, potassium phosphate, acid pyrophosphate, polyphosphate, etc., and a natural antioxidant such as polyphenol, catechin, α-tocopherol, rosemary extract, vitamin C, green tea extract, licorice extract, chitosan, tannic acid, phytic acid, etc. When used as a feed, the composition may be formulated into a common feed form and may contain common feed ingredients.

The feed additive and feed may further contain a dried ingredient selected from a grain, e.g., ground or crushed wheat, oats, barley, corn or rice, a vegetable protein feed, e.g., a feed having rape, bean and sunflower as main ingredients, an animal protein feed, e.g., blood meal, meat meal, bone meal or fish meal, a sugar, a dairy product, e.g., powdered milk or whey powder, etc., and may further contain a nutritional supplement, a digestion- and absorption-improving agent, a growth-promoting agent, etc.

The feed additive may be administered to an animal either alone or in combination with another feed additive in an edible carrier. In addition, the feed additive may be easily administered to an animal by directly mixing with an animal feed as a top dressing or as an oral formulation separately from the feed. When the feed additive is administered separately from the animal feed, it may be prepared as an immediate or sustained release formulation in combination with a sitologically acceptable edible carrier, as well known in the art. The edible carrier may be solid or liquid, for example, cornstarch, lactose, sucrose, bean flake, peanut oil, olive oil, sesame oil and propylene glycol. When a solid carrier is used, the feed additive may be a tablet, a capsule, a powder, a troche, a sugar-coated tablet or a non-dispersed top dressing. When used as a liquid carrier, the feed additive may be a soft gelatin capsule, a syrup, a suspension, an emulsion or a solution.

In addition, the feed additive and the feed may contain an adjuvant, e.g., a preservative, a stabilizer, a wetting agent, an emulsifier, a solubilizer, etc. The feed additive may be used by adding to an animal feed by spraying or mixing.

The feed or feed additive of the present disclosure may be applied to animal feeds for mammals, poultry and fish.

It may be used for mammals such as pig, cow, sheep, goat, experimental rodents, pets (e.g., dog or cat), etc., poultry such as chicken, turkey, duck, goose, pheasant, quail, etc., and fish such as trout, etc., although not being limited thereto.

The feed or feed additive of the present disclosure may be used in animal feeds for enhancing the growth, immunity, etc. of animals.

The amount of the *Lactobacillus sakei* strain contained in the composition according to the present disclosure may be about $10^6$-$10^{12}$ CFU/mL, e.g., $10^7$-$10^{11}$ CFU/mL or $10^8$-$10^{10}$ CFU/mL, for a single administration. Specifically, the strain may be administered in the form of live bacteria, and may be killed or attenuated before administration. In addition, when the composition is prepared using a supernatant of a culture, it may pass through an additional sterilization process by heating. The amount of the strain necessary to provide minimum effect may vary depending on the physical or health condition of a subject. In general, a daily administration dosage may be about $10^6$-$10^{12}$ CFU/mL, e.g., $10^7$-$10^{11}$ CFU/mL or $10^8$-$10^{10}$ CFU/mL.

In another aspect, the present disclosure provides a method for preparing a composition for preventing, alleviating or treating an autoimmune disease, which includes:

(a) a step of preparing a *Lactobacillus sakei* strain; and (b) a step of culturing the strain in a culture medium.

In a specific exemplary embodiment of the present disclosure, the preparation method further includes a step of isolating extracellular vesicles derived from the *Lactobacillus sakei* strain in the culture medium.

In another aspect, the present disclosure provides a method for preparing a composition for preventing, alleviating or treating an autoimmune disease, which includes a step of preparing extracellular vesicles derived from a *Lactobacillus sakei* strain.

Advantageous Effects

The features and advantages of the present disclosure may be summarized as follows:

(i) The present disclosure provides a composition for preventing, alleviating or treating an autoimmune disease, which contains *Lactobacillus sakei*, a culture, lysate, extract or fermentation product thereof, or extracellular vesicles derived from *Lactobacillus sakei* or a culture, lysate, extract or fermentation product thereof as an active ingredient.

(ii) Since the *Lactobacillus sakei* or the extracellular vesicles contained in the composition of the present disclosure inhibit proinflammatory factors that cause various autoimmune diseases (e.g., TNFα, autoantibodies, collagen, antigen-specific IgGs, etc.) or increase the proportion of immunosuppressive cells (e.g., tolDC cells, Tregs, etc.), they can be used effectively for the prevention or treatment of autoimmune diseases.

BEST MODE

Hereinafter, the present disclosure will be described in more detail through examples. The examples are provided only to describe the present disclosure more specifically and it will be obvious to those having ordinary knowledge in the art that the scope of the present disclosure is not limited by the examples.

EXAMPLES

Materials and Methods

1. Preparation of *Lactobacillus sakei* LBML6 Strain

A *Lactobacillus sakei* LBML6 strain deposited in the Korean Culture Center of Microorganisms on Jun. 15, 2021 with the accession number KCCM13011P was inoculated to 30 mL of an MRS broth medium to 0.1% and cultured at 30° C. for 18 hours. Then, after conducting centrifugation at 3500 rpm for 10 minutes, the remaining medium was removed by washing the bacteria 3 times with PBS.

2. Preparation of Experimental Animals

A model of rheumatoid arthritis, which is one of autoimmune diseases, of DBA-1J mice was prepared using bovine collagen.

3. Administration of Test Substances

Adequate amounts of test substances were prepared by diluting in a vehicle. Test groups and administration dosage are as shown in Table 1.

TABLE 1

| Group | Sex | Number of animals | Induction of arthritis | Test substance | Administration dosage (μL/head) |
|---|---|---|---|---|---|
| Normal | M | 5 | N | PBS | 200 |
| CIA | M | 10 | Y | PBS | 200 |
| CIA + strain | M | 10 | Y | LBML6 | 200 |

The test substances were administered orally for 7 weeks, at 200 μL/head, 5 times/week. Only physiological saline was administered for a control group. For the oral administration, the animal was fixed by the cervical skin fixation method and the test substance was administered directly into the stomach using an oral zonde.

The test groups were Normal (control; PBS), CIA (induction of arthritis+PBS) and CIA+strain (induction of arthritis+strain of the present disclosure).

4. Isolation of EVs

Figure 6:
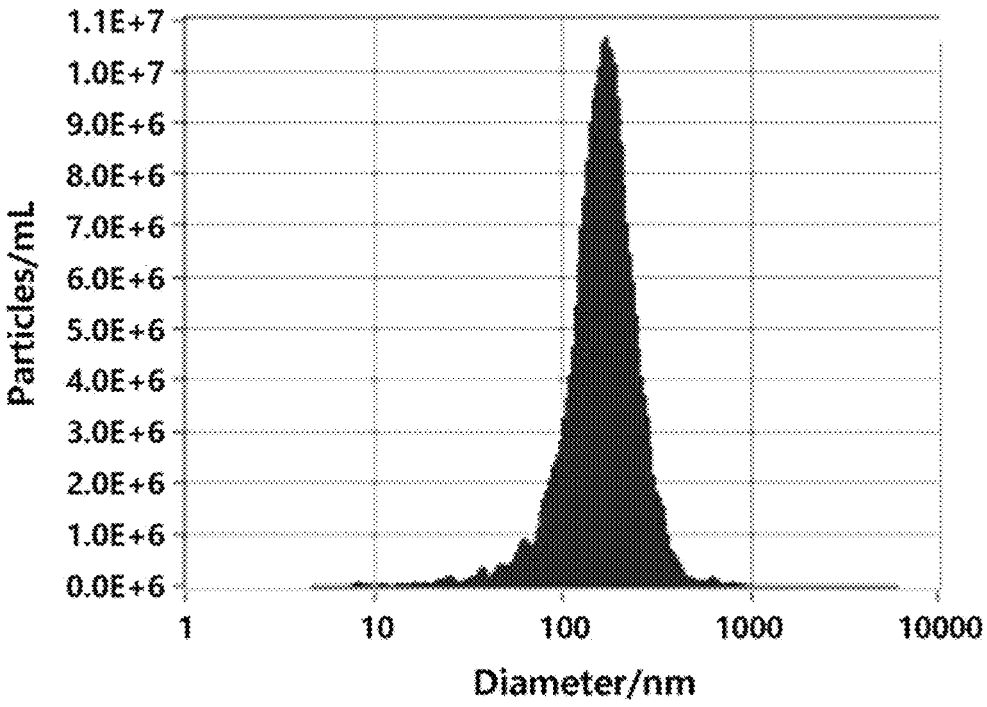
FIG. 6 shows the size of EVs isolated from a *Lactobacillus sakei* LBML6 strain.
Figure 7:
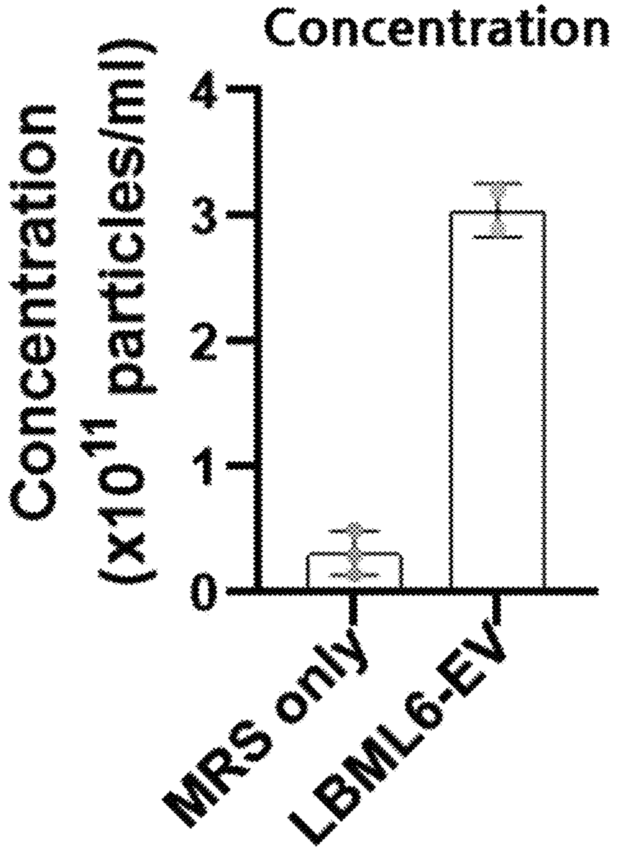
FIG. 7 shows the concentration of EVs isolated from a *Lactobacillus sakei* LBML6 strain.

*Lactobacillus sakei* (LBML6) was inoculated to 30 mL of an MRS broth medium to 0.1% and cultured at 30° C. for 18 hours. Then, after conducting centrifugation at 3500 rpm and 4° C. for 10 minutes and then at 10,000×g and 4° C. for 20 minutes, the supernatant was recovered and then filtered through a 0.22-μm filter to remove the bacteria. After mixing the supernatant with a 1 M NaCl solution of 16% PEG6000, reaction was conducted at 4° C. for 15 hours. Then, EV pellets were obtained by conducting centrifugation at 10,000×g and 4° C. for 20 minutes. The obtained EV pellets were resuspended in a 0.5 M NaCl solution of 5% PEG6000 and then centrifuged at 11,000 rpm and 4° C. for 20 minutes after washing. The pellets were resuspended in PBS to finally isolate EVs derived from *Lactobacillus sakei* (LBML6). The size (FIG. 6) and concentration (FIG. 7) of the isolated EVs were measured using Zetaview (Particle Metrix GmbH).

5. Differentiation of Immature Dendritic Cells from Bone Marrow

Monocytes were isolated from the mouse (Orient Bio, Balb/c, female 6 wk) bone marrow cells of the femur and tibia through centrifugation using the Ficoll gradient method (Hlozkova, K., Starkova, J. Assessment of the Metabolic Profile of Primary Leukemia Cells. *J. Vis*. Exp. (141), e58426, doi: 10.3791/58426 (2018)). The isolated monocytes were prepared onto a 6-well plate at a concentration of $2\times10^6$ cells/well and treated with 20 ng/ml GM-CSF and 10 ng/ml IL-4 in a medium (RPMI) containing fetal bovine serum (FBS). Then, the cells were cultured for 6 days. On day 3, differentiated immature dendritic cells were obtained by replacing the medium with a fresh medium containing cytokines.

6. Differentiation of Mature Dendritic Cells

In order to differentiate the obtained immature dendritic cells (DCs) into mature dendritic cells (DCs), differentiation into mature dendritic cells and activation were induced by treating with LPS (positive control) for 2 hours. Then, the cells were co-cultured with the *Lactobacillus sakei* (LBML6) or the EVs derived from *Lactobacillus sakei* (LBML6) at MOI of 1 and 10, respectively, for 24 hours as secondary stimulants.

7. Co-Culturing with T Cells

CD3+ T cells stained with CFSE isolated from mouse spleen (Invitrogen) were co-cultured with the dendritic cells cultured for 24 hours with *Lactobacillus sakei* (LBML6) at a ratio of 1:1, for 3 days. In order to evaluate whether the activity of T cells was inhibited by the tolDCs, the degree of T cell division and the amount of secreted cytokines (IFN-γ and IL-17) were identified using a CBA assay kit (BD Th1/2/17 CBA kit). The culture medium used for the co-culturing was stored and used for application to an in-vitro model of psoriasis.

8. Preparation of Psoriatic Model of Human Keratinocytes $4\times10^5$ HaCaT cells (CLS) were seeded on a 6-well plate. When the cells were attached, they were treated with $CaCl_2$) (Sigma) for 4 hours and then with imiquimod (IMQ, Calbiochem) for induction of inflammation. 24 hours later, the culture medium in 5 was treated to each well. 24 hours later, the cells were collected and RNAs were isolated for measurement of gene expression.

9. Measurement of Gene Expression (qPCR)

For measurement of gene expression, the RNAs of the cells were synthesized into cDNAs using reverse thranscriptases and dNTPs of a cDNA synthesis kit (Thermo). The genes were amplified using primers (Macrogen).

EXPERIMENTAL RESULTS

Example 1. Measurement of Arthritis Incidence Rate and Arthritis Score in Collagen-Induced Arthritic Mouse Model Measurement of arthritis score: The degree of arthritis was scored according to the criteria presented in Table 2, immediately before and three times a week after administration of the test substance. The scores for the limbs were added together (maximum: 16 points).

TABLE 2

| Score | Status |
|---|---|
| 0 | No edema or swelling |
| 1 | Mild edema and redness localized to joints |
| 2 | Mild edema and redness from joints to carpal and tarsal bones |
| 3 | Severe edema and redness from joints to carpal and tarsal bones |
| 4 | Overall edema and redness and joint stiffness observed |

Figure 1:
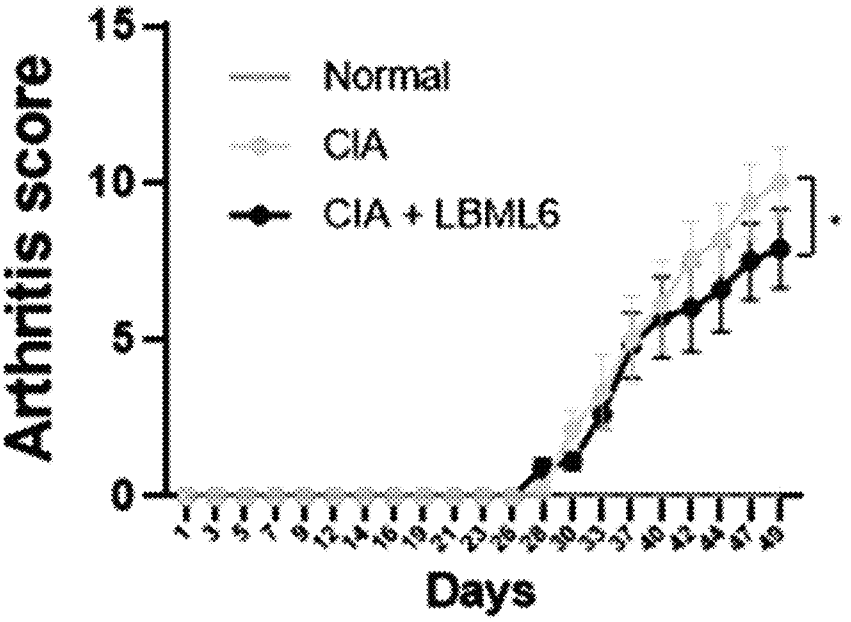
FIG. 1 shows a result of measuring arthritis score and incidence rate after orally administering a *Lactobacillus sakei* LBML6 strain to a collagen-induced arthritic mouse model for 7 weeks.

The result of measuring arthritis score and arthritis incidence rate while orally administering the *Lactobacillus sakei* LBML6 strain to a collagen-induced arthritic mouse model for 7 weeks is shown in FIG. 1.

As a result, the collagen-induced arthritic control group showed the highest incidence rate and arthritis score and the group treated with the *Lactobacillus sakei* LBML6 strain showed significant decrease in the incidence rate and arthritis score.

Figure 2:
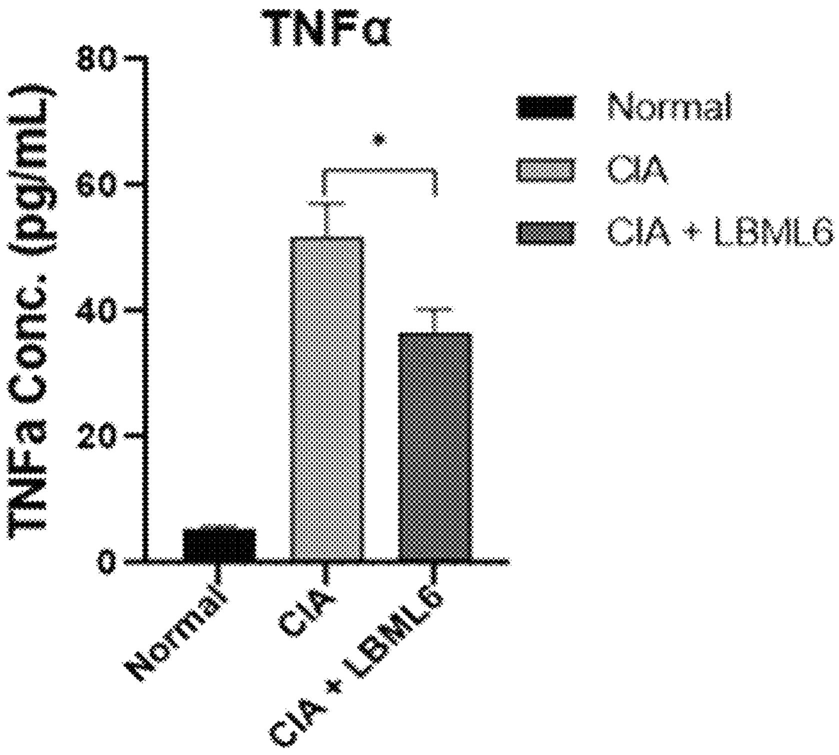
FIG. 2 shows a result of measuring the concentration of the proinflammatory cytokine TNFα in blood taken from an experimental animal.

Example 2. Measurement of Concentration of TNFα and Collagen Antigen-Specific IgG in Blood The concentration of the proinflammatory cytokines TNFα and collagen-specific IgG in the blood of the experimental animal was measured. FIG. 2 shows the result of measuring the concentration of TNFα, and FIG. 3 shows the result of measuring the concentration of collagen antigen-specific IgG.

Figure 3:
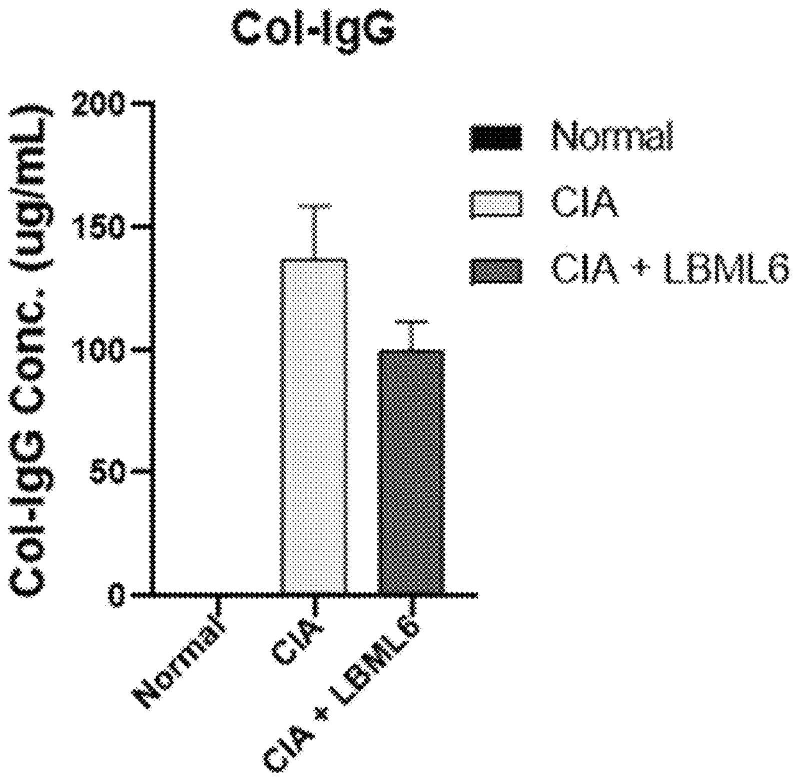
FIG. 3 shows a result of measuring the concentration of collagen-specific IgG in blood taken from an experimental animal.

As shown in FIGS. 2 and 3, the production of TNFα and IgG in blood was promoted when arthritis was induced as compared to the normal group and it was confirmed that the concentration of TNFα and IgG was decreased when the *Lactobacillus sakei* LBML6 strain was administered to the experimental animal.

Example 3. Measurement of Immunosuppressive Cells in Intestinal Lymph Node

Figure 4:
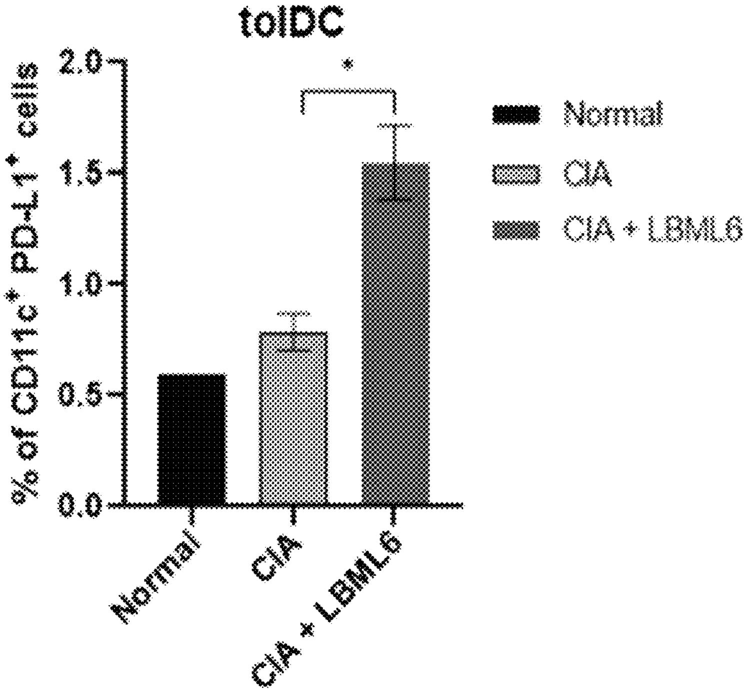
FIG. 4 shows a result of measuring the proportion of tolerogenic dendritic cells (tolDCs) that suppress immunity in the intestinal lymph node.

The proportion of tolerogenic dendritic cells (tolDCs) and regulatory T cells (Tregs) that suppress immunity in the intestinal lymph node was investigated. FIG. 4 shows the result of measuring the proportion of tolDCs, and FIG. 5 shows the result of measuring the proportion of Tregs.

Figure 5:
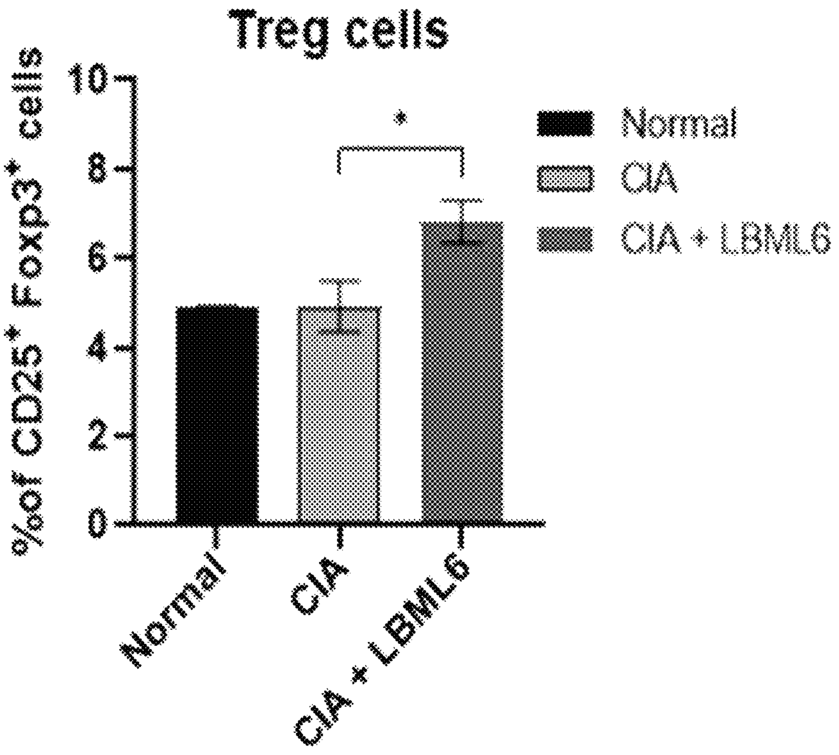
FIG. 5 shows a result of measuring the proportion of regulatory T cells (Tregs) that suppress immunity in the intestinal lymph node.

As shown in FIGS. 4 and 5, the proportion of the tolDC cells and Treg cells that suppress immunity in the intestinal lymph node was increased when the *Lactobacillus sakei* LBML6 strain was administered as compared to the normal group or the arthritis-induced control group.

Example 4. Psoriasis-Alleviating Efficacy of LBML6

Figure 8:
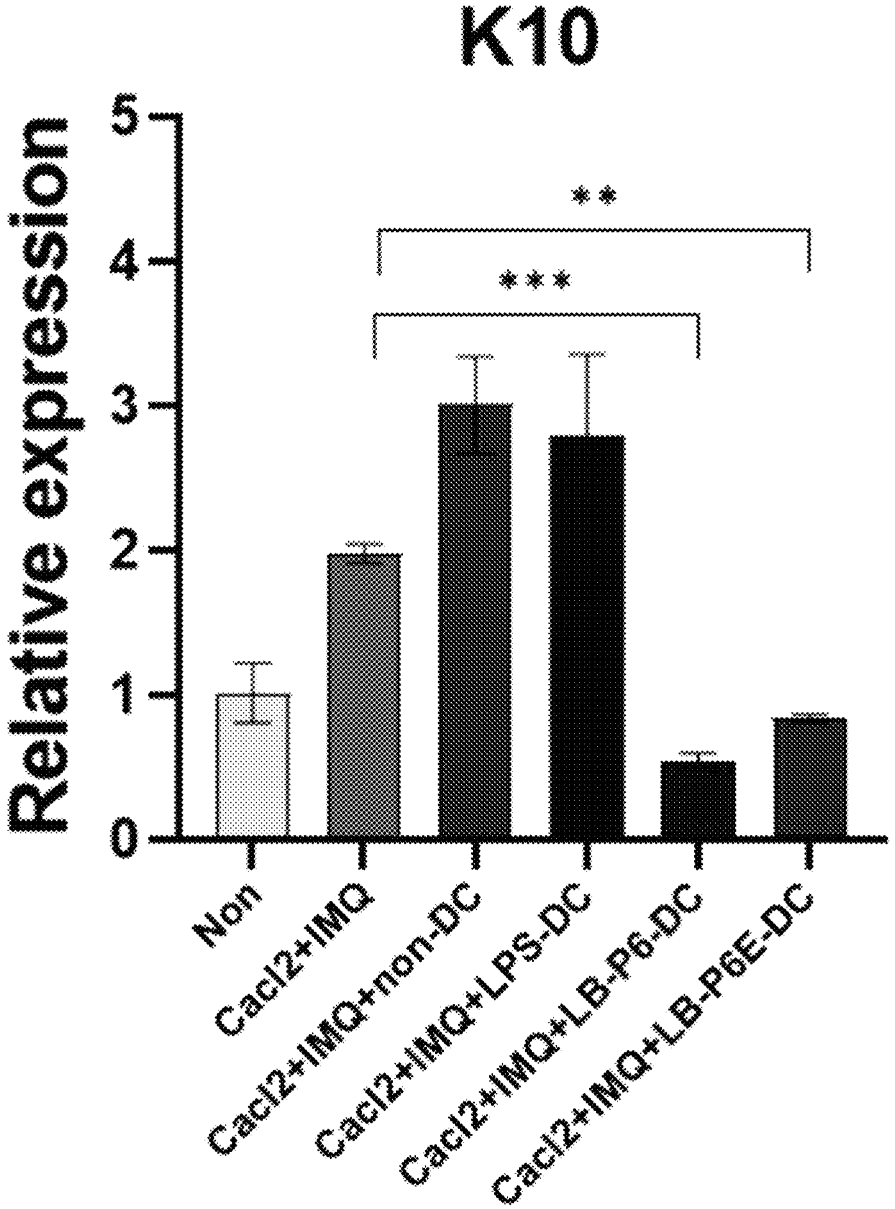
FIG. 8 shows a result of investigating the expression of the division marker K10 in skin cells treated with a *Lactobacillus sakei* LBML6 strain or EVs isolated therefrom.
Figure 9:
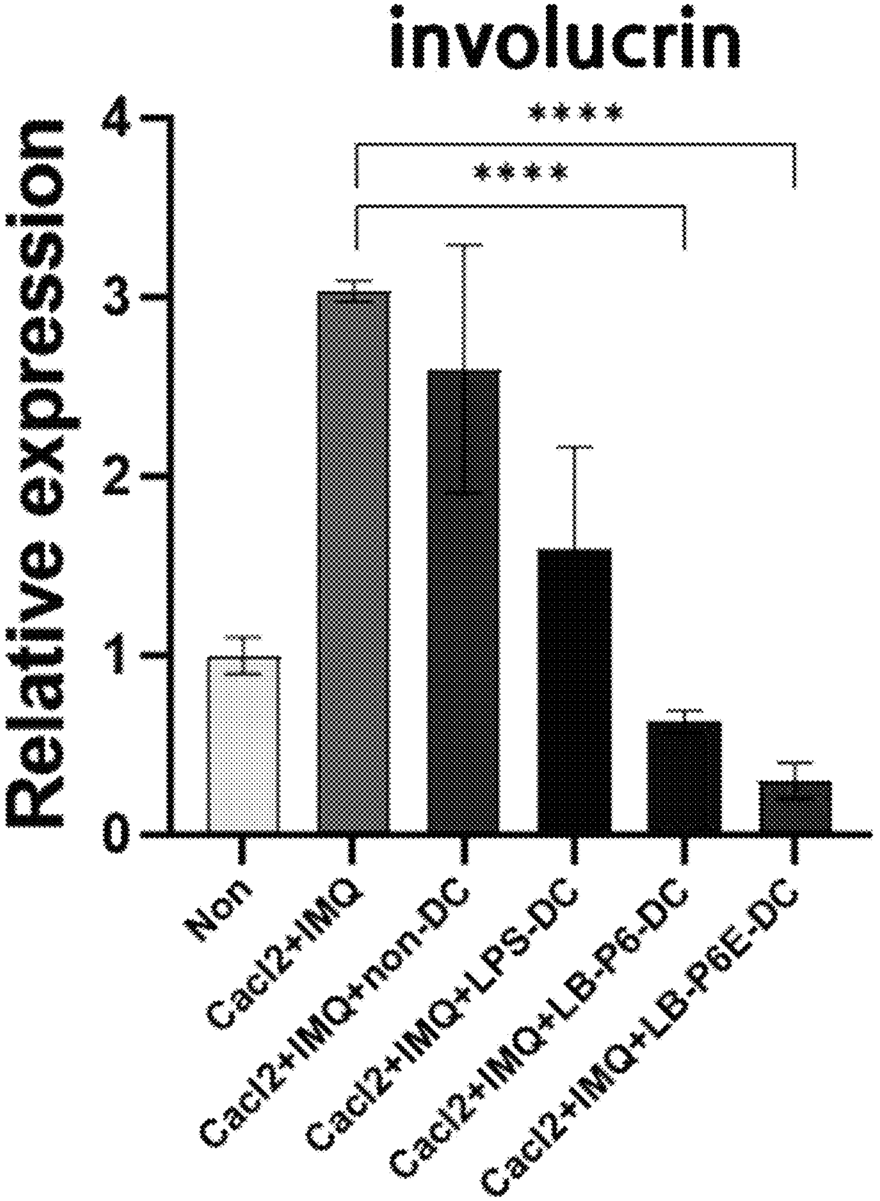
FIG. 9 shows a result of investigating the expression of the division marker involucrin in skin cells treated with a *Lactobacillus sakei* LBML6 strain or EVs isolated therefrom.
Figure 10:
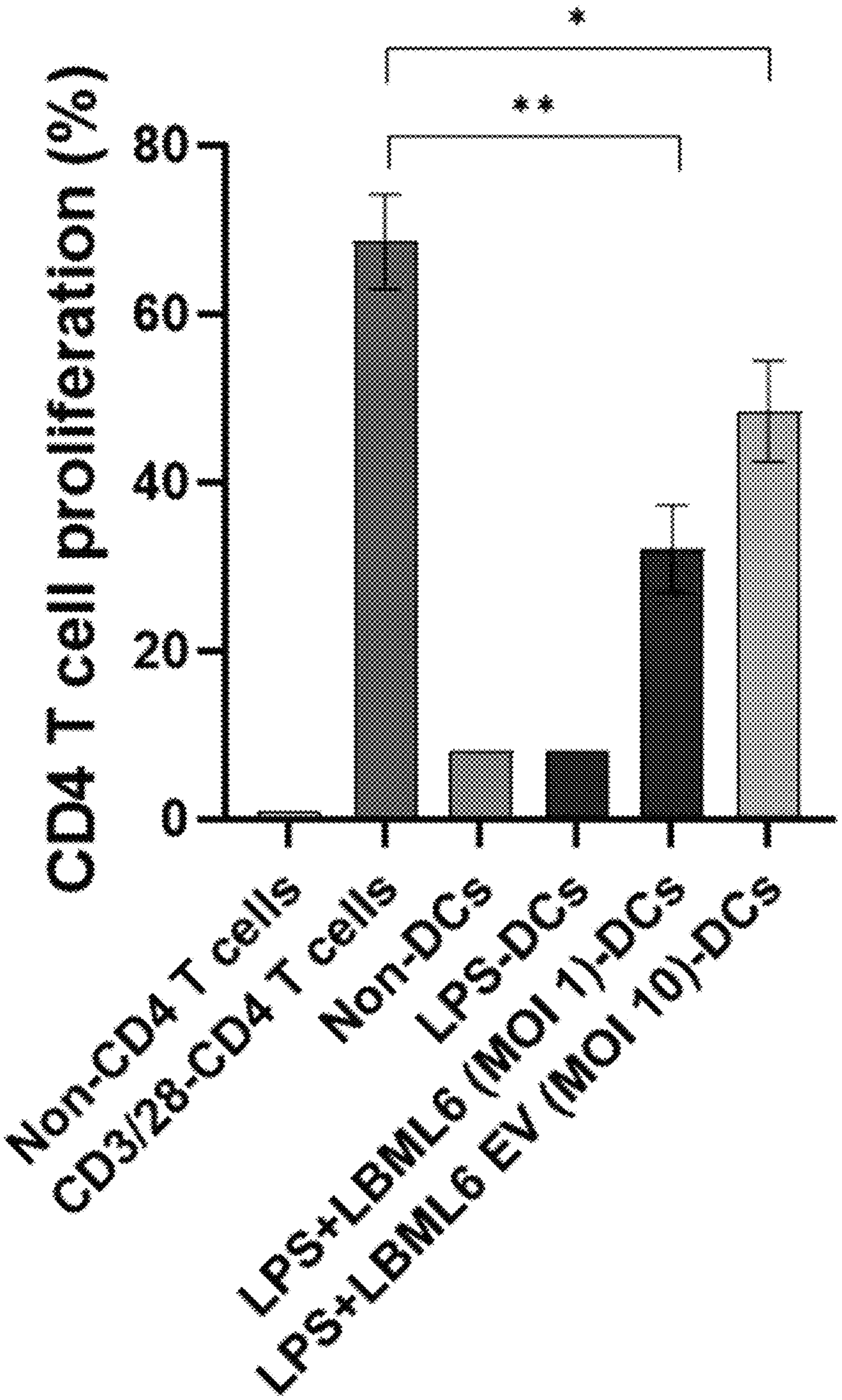
FIG. 10 shows a result of investigating whether the activity of CD4 T cells is inhibited by treatment with a *Lactobacillus sakei* LBML6 strain or EVs isolated therefrom.

HaCaT cells may be transformed into keratinocytes by inducing cell division and inflammation by treating with $CaCl_2$) and IMQ. As a result of investigating the expression of the division markers K10 (FIG. 8) and involucrin (FIG. 9) in the skin cells, it was confirmed that the gene expression was decreased significantly in the cells treated with the LBML6 (MOI 1) and LBML6 EVs, indicating that the division of the skin cells was inhibited.

Example 5. Effect of Inhibiting CD4 T Cell Activity

It is known that the increased division of CD4 T cells activates T cells and is involved in various inflammatory responses. In order to determine whether the tolDCs induced by the EVs derived from *Lactobacillus sakei* can directly inhibit the activity of CD4 T cells, tolDCs induced by *Lactobacillus sakei* (LBML6) and *Lactobacillus sakei*-derived EVs were co-cultured with CD4 T cells stained with CFSE at a ratio of 1:1 for 3 days. 3 days later, the co-cultured cells were collected and the degree of reduction of CFSE was measured.

The T cells co-cultured with the LPS-treated dendritic cells showed nearly 90% of division. However, the cell division was suppressed by about 60% for the T cells co-cultured with the dendritic cells treated with the *Lactobacillus sakei*-derived EVs. This means that the tolDCs induced by the *Lactobacillus sakei*-derived EVs can reduce immune response by directly inhibiting the activity of CD4 T cells.

From these results, it can be confirmed that *Lactobacillus sakei* (LBML6) and *Lactobacillus sakei* (LBML6)-derived EVs can reduce immune response by inhibiting the activity of CD4 T cells through reduced DC activity. Accordingly, they can regulate various autoimmune diseases including rheumatoid arthritis.

Although the present disclosure was described using the examples, those having ordinary knowledge in the art will be able to change and modify the present disclosure without departing from the technical idea of the present disclosure and such changes or modifications are also included in the scope of the present disclosure.

ACCESSION NUMBERS

Depository agency: Korean Culture Center of Microorganisms (overseas)
Accession number: KCCM13011P
Date of deposition: 20210615
Depository agency: Korean Culture Center of Microorganisms (overseas)
Accession number: KCCM12654P
Date of deposition: 20200114
Depository agency: Korea Research Institute of Bioscience and Biotechnology
Accession number: KCTC13818BP
Date of deposition: 20190307

The invention claimed is:

1. A method for alleviating or treating an autoimmune disease in a subject in need thereof, comprising administering a therapeutically effective amount of: *Lactobacillus sakei*, a culture, lysate, extract or fermentation product thereof; or extracellular vesicles derived from the *Lactobacillus sakei*, to the subject, wherein the *Lactobacillus sakei* is a *Lactobacillus sakei* LBML6 strain deposited with the accession number KCCM13011P, and wherein the administration of the *Lactobacillus sakei*, the culture, lysate, extract or fermentation product thereof; or the extracellular vesicles derived from the *Lactobacillus sakei* reduces immune response in the subject.

2. The method according to claim 1, wherein the autoimmune disease is selected from a group consisting of psoriatic dermatitis, alopecia areata, asthma, conjunctivitis, periodontitis, rhinitis, otitis media, pharyngitis, tonsillitis, Crohn's disease, ankylosing spondylitis, lupus, psoriatic arthritis, osteoarthritis, rheumatoid arthritis, periarthritis of shoulder, tendonitis and multiple sclerosis.

3. The method according to claim 1, wherein the *Lactobacillus sakei* or the culture, lysate, extract or fermentation product thereof comprises the extracellular vesicles of *Lactobacillus sakei.*

4. The method according to claim 1, wherein the extracellular vesicles have a diameter of 10-1,000 nm.

5. The method according to claim 3, wherein the extracellular vesicles have a diameter of 10-1,000 nm.

6. A method for preparing a composition for alleviating or treating an autoimmune disease, comprising:

(a) a step of preparing a *Lactobacillus sakei* strain; and (b) a step of culturing the strain in a culture medium, wherein the *Lactobacillus sakei* is a *Lactobacillus sakei* LBML6 strain deposited with the accession number KCCM13011P.

7. A *Lactobacillus sakei* LBML6 strain deposited with the accession number KCCM13011P.

* * * * *